United States Patent [19]

Liebig et al.

[11] 4,047,252
[45] Sept. 13, 1977

[54] DOUBLE-VELOUR SYNTHETIC VASCULAR GRAFT

[75] Inventors: William J. Liebig, Franklin Lakes; German Rodriguez-M, Bergenfield, both of N.J.

[73] Assignee: Meadox Medicals, Inc., Oakland, N.J.

[21] Appl. No.: 653,680

[22] Filed: Jan. 29, 1976

[51] Int. Cl.² .............................................. A61F 1/24
[52] U.S. Cl. ......................................... 3/1.4; 66/195; 66/196
[58] Field of Search .................... 3/1.4, 1; 128/334 R

[56] References Cited

U.S. PATENT DOCUMENTS

| | | | |
|---|---|---|---|
| 2,836,181 | 5/1958 | Tapp | 3/1.4 |
| 3,805,301 | 4/1974 | Liebig | 3/1.4 |
| 3,878,565 | 4/1975 | Sauvage | 3/1.4 X |
| 3,945,052 | 3/1976 | Liebig | 3/1.4 |

FOREIGN PATENT DOCUMENTS

| | | | |
|---|---|---|---|
| 2,461,370 | 7/1975 | Germany | 3/1.4 |

OTHER PUBLICATIONS

"Life Extenders" (Pamphlet), by U.S. Catheter & Instrument Corp., a C. R. Bard Co., Box 787, Glens Falls, New York, 12801, published 1971, Vasculour-D Prosthesis Relied Upon.

Primary Examiner—Ronald L. Frinks
Attorney, Agent, or Firm—Blum, Moscovitz, Friedman & Kaplan

[57] ABSTRACT

A double-velour vascular graft has a tubular body or trellis with loops projecting both outwardly and inwardly from said trellis. The loops on both the inner and outer surfaces of the trellis provide for more effective preclotting and ingrowth of tissue without impeding the flow of blood through the tubular body. The graft is produced on a double-needle bar warp-knitting machine using two outside beams and two inside beams, the beams feeding yarn for the loops to said knitting machine at a greater rate than the beams feeding yarn for the trellis.

30 Claims, 3 Drawing Figures

DOUBLE-VELOUR SYNTHETIC VASCULAR GRAFT

BACKGROUND OF THE INVENTION

Vascular grafts of synthetic fiber are now widely used, a variety of constructions in a variety of materials being available. A principal factor in the selection of a particular graft is the porosity of the fabric of which the graft is composed. This factor is significant because the porosity controls both the tendency to hemorrhage and the ingrowth of tissue into the wall of the graft.

The general procedure for implantation of a graft includes the step of preclotting, a step in which the graft is immersed in the blood of the patient and then allowed to stand for a period long enough for clotting to ensue. As a result, when the graft is implanted surgically hemorrhaging does not occur; yet, growth of tissue into the wall of the graft can proceed. This growth is extremely important since, eventually, the wall of the graft simulates the wall of the vessel which it replaces and, if all goes properly, provides a lumen which remains open and free of clots.

The degree of adhesion of tissue to the wall of the graft varies with the material used. Thus, V. J. Lombardi in U.S. Pat. No. 3,561,441 discloses the use of a non-sticking material having loops thereon for use in convering and treating wounds. The material which he proposes to use is a polyfluorinated polyolefin in filament, spun or plastic ribbon form. Lombardi discloses that, as the result of using a non-sticking material, the fabric can be removed from a wound periodically as a step in the changing of the dressing without tearing open the wound itself.

L. R. Sauvage in U.S. Pat. No. 3,878,565 has disclosed a tubular textile synthetic cardio-vascular prosthesis of polyester or other synthetic fibers, the prosthesis consisting of a body having a multiplicity of fiber loops extending outwardly from the surface thereof. Also, as shown in his FIG. 2A, the body is crimped into irregular, circumferential corrugations. Such corrugations are intended to provide protection against kinking or collapse of the tubing and narrowing of the lumen thereof as the result of bending or other factors. However, the degree of protection afforded by such irregular corrugations varies over the length of the tube and can be below the required level of protection as the result of the corrugations being so irregular in shape and size.

While the construction of Sauvage facilitates growth of tissue exterior to the body or trellis of the tubular graft, the absence of loops on the interior of the tubing may result in exposure of the synthetic filaments of which the tubing is composed. Furthermore, the Sauvage graft is circularly-knit so that the technique which provides the fabric loops on the Sauvage graft is not applicable to warp-knit tubing.

As is evident, it would be desirable that a graft tubing be provided which has uniform strength and rigidity along its entire length, which is suitable for bifurcation and which facilitates growth of tissue along the interior thereof as well as on the outer surface thereof.

SUMMARY OF THE INVENTION

A synthetic vascular graft is warp-knit from a fiber or filament to which growing tissue can adhere. A preferred fiber is polyester, and an especially preferred fiber is that sold under the tradename of Dacron by Dupont. However, it is to be understood that any comparable fiber and, especially polyester fiber or yarn is to be included as a suitable alternate or substitute.

In order to facilitate growth of tissue over the interior of the tubing as well as the exterior thereof, fiber loops are provided on the interior as well as the exterior of the graft tubing. In order to avoid interference with the flow of blood through the lumen of said tubing, the fiber loops on the interior are shorter, i.e., smaller than those on the exterior thereof. Conveniently, the extent to which the exterior loops protrude is greater than that to which the interior loops protrude by a factor between 3 and 10. Preferably, the factor is between 4 and 7. The loops constitute a pile mat. Hereinafter the term "loops" will refer only to those protruding inwardly or outwardly from the trellis.

In warp-knitting the synthetic vascular graft two outside beams and two inside beams are used. Where the outside beams feed yarn for loops and the inside beams feed yarn for the trellis, yarn is fed from the outside beams at a greater rate than from the inside beams, the ratio of the rates lying between 1.75:1 and 4.50:1. The synthetic vascular graft tubing, after knitting, is compacted and crimped in a regular, circular corrugation. The warp-knit material is preferably, but not necessarily of the locknit structure or the tricot structure, such as is shown in the Figures of U.S. Ser. No. 435,131 now U.S. Pat. No. 3,945,052.

Bifurcated double-velour grafts can be warp-knit by the method of the present invention.

Accordingly, an object of the present invention is a warp-knit, double-velour, synthetic vascular graft which facilitates formation of tissue on the exterior and interior surfaces thereof without impeding the flow of blood therethrough.

Another object of the present invention is a warp-knit, double-velour, synthetic vascular graft which is of a material to which tissue can adhere readily.

A further object of the present invention is a method of preparing a warp-knit, double-velour, synthetic vascular graft wherein loops on the exterior of said fabric extend outwardly further than loops on the interior of said fabric extend inwardly.

A significant object of the present invention is a method of preparing a warp-knit, double-velour synthetic vascular graft in which said graft is compacted and corrugated and has uniform strength throughout.

A particularly important object of the present invention is a method of preparing a warp-knit, double-velour, vascular graft which can be bifurcated.

Still other objects and advantages of the invention will in part be obvious and will in part be apparent from the specification.

The invention accordingly comprises the several steps and the relation of one or more of such steps with respect to each of the others, and the article possessing the features, properties, and the relation of elements, which are exemplified in the following detailed disclosure, and the scope of the invention will be indicated in the claims.

BRIEF DESCRIPTION OF THE DRAWINGS

For a fuller understandng of the invention, reference is had to the following description taken in connection with the accompanying drawings, in which.

DESCRIPTION OF THE PREFERRED EMBODIMENTS

Figure 1:
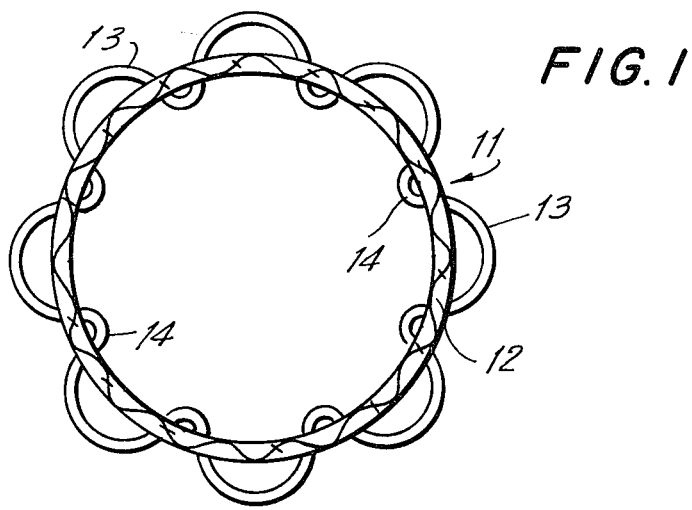
FIG. 1 is a transverse sectional view of a graft in accordance with the present invention.
Figure 2:
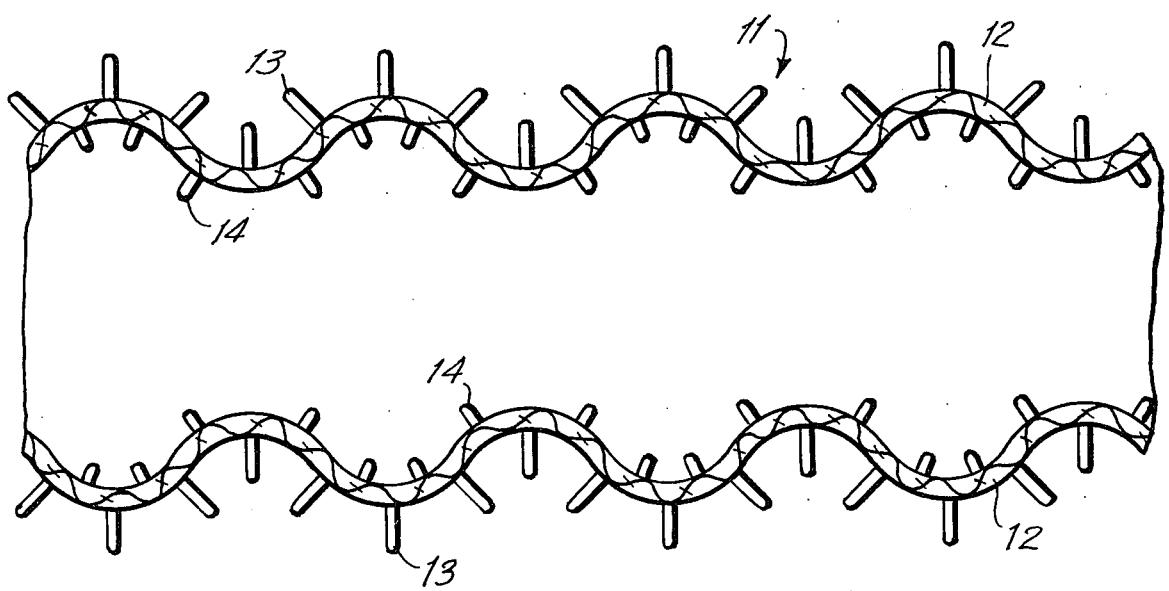
FIG. 2 is a longitudinal section of said vascular graft.

A double-velour synthetic vascular graft in accordance with the present invention is shown in transverse section in FIG. 1 and in longitudinal section in FIG. 2. The double-velour fabric is indicated generally by the reference numeral 11, the body or the trellis having the reference numeral 12, the outwardly extending loops having the reference numeral 13 and the inwardly extending loops having the reference numeral 14. As is evident from the Figures, loops 13 extend outwardly substantially more than loops 14 extend inwardly. It has been found desirable that loops 13 extend from the surface from three to 10 times as far as loops 14 extend. Preferably, loops 13 should extend from four to seven times as far as loops 14. The loops extend inwardly to a smaller distance than those on the exterior surface in order to avoid interfering seriously with the flow of blood through the lumen of the graft. Nevertheless, inward extension is desirable so that tissue may grow therein and eventually present what is essentially a surface of tissue to the blood flowing through the graft. The outwardly extending loops also serve for tissue ingrowth.

Figure 3:
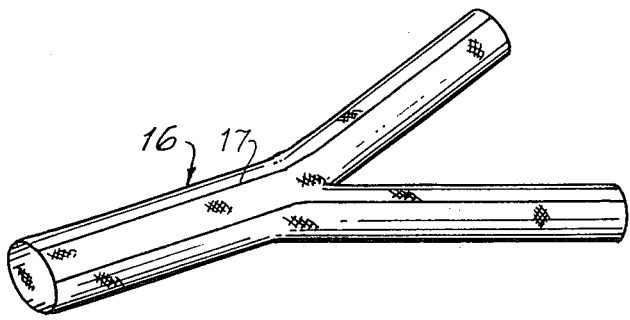
FIG. 3 is a view in perspective of a bifurcated synthethic vascular graft in accordance with the present invention.

As is evident from FIG. 2, it is desirable that the graft be corrugated along its length in a regular, circular crimp, the result being a rigidity which is sufficient to prevent collapse of the tube and which resists pressure uniformly over the entire length of the tube. Further, as is evident from FIG. 3, a bifurcated graft indicated generally by the reference numeral 16 lies within the scope of the invention.

As is well-known, the porosity of the graft must be carefully controlled. In general, it has been found that after knitting, it is desirable to compact the graft, such compacting preferably being carried out chemically by techniques such as is disclosed in copending application Ser. No. 448,447, filed Mar. 5, 1974, now U.S. Pat. No. 3,986,828 and assigned to the same assignee, or by other suitable means.

In describing the yarns of the graft of the present invention, the term "total count" will, where appropriate, be used for yarns having one-ply or more than one-ply, regardless of the count of the individual plys.

The double-velour synthetic vascular graft of the present invention is made on a warp-knitting machine using a double needle bar. A preferred number of needles per inch is from about 18 to about 36. On the basis of porosity of the product, and ease of manufacture about 28 needles per inch are particularly suitable. The trellis of the graft is made from a yarn having count from 30 to 150 denier. A preferred range of yarn counts for the trellis is 30 to 70, and a particularly suitable yarn count is about 40 denier. The trellis yarn is preferably single ply, but can be double ply. Where double ply yarn is used, the total count is then 30 to 150 denier, preferably 30 to 70 and optimally 40 denier. Further, it can be stated that multi-ply yarn can be used so long as the total counts fall within the ranges specified. The term "multi-ply" is used herein to indicate more than two-ply.

In one method of making the trellis, the yarn is fed from two inside beams, each beam being a spool holding a plurality of ends. In this method, two outside beams may be used in conjunction with the inside beams, the outside beams being used for making the loops, each outside beam also having a plurality of ends. However, it should be noted that the inside beams may be used for making the loops and the outside beams used for making the trellis. Regardless of which beams are used for the trellis and which for the loops, non-texturized yarn is used for the trellis and texturized yarn is used for the loops. In general, the yarn count for the loops should be at least as great as that of the trellis yarn count. The minimum number of beams used in making the double-velour material of the present invention is 4. However, a greater number of beams may be found useful for specific applications.

The loops are preferably made of either single-ply yarn or double-ply yarn, but multi-ply yarns may also be used. Where double-ply yarn is used, the porosity is lower of course. Also, with double-ply yarn the yarn count is twice that of the individual plys. Where single-ply yarn is used for making the loops, in general, the yarn count should be between 30 and 150 denier, with a preferred range being 30 to 70 denier. A particularly suitable yarn count for the loops is 40 denier. Where the loops are to be double-ply with the objective of lowering the porosity, the yarn count for the individual plys are exactly the same as for the single ply, but the totals, of course, are double. Thus, the yarn counts, as totals, are, in general, 60 to 300, 60 to 140 for the preferred range and 80 as a particularly suitable count. Where multi-ply yarns are used for the loops, the total count ranges correspond to those for the double-ply yarns.

The extent to which the loops project from the trellis is automatically established when the relative feed rates of the loop and trellis yarns are selected and the ratio of the extents to which the loops protrude inwardly and outwardly from the trellis is established.

In order that the loops may project from both sides of the trellis, the yarn from the beams providing the loop yarn is fed at a higher rate than that for the trellis. The ratio of the rates lies in the range from 1.75:1 to 4.50:1. Such rates produce a graft having a ratio of the loop yarn length to trellis yarn length lying between 1.75 and 4.50.

As aforenoted, the yarn, preferably, may be knitted either in the locknit construction or in the tricot construction.

Preferably, subsequent to knitting, the fabric is subjected to compacting in order to decrease the size of the openings, and, thereby, the porosity of the fabric. The texturized yarns possess a different shrinkage characteristic from the non-texturized yarns.

Subsequent to compacting, the graft is crimped. A preferred method of crimping is disclosed in the copending application Ser. No. 638,580 assigned to the same assignee and filed on Dec. 8, 1975. Crimping in accordance with the method disclosed in said application results in uniform, regular, circular corrugations which provide uniform strength over the entire surface of the graft tubing, thus virtually guaranteeing that no section or region presents the possibility of kinking or collapsing under pressure.

Where a less porous material is desired, the beams which feed the yarn for the loops are charged with two-ply texturized yarn. For the less porous material 60 – 90 courses per inch after compaction are found to be satisfactory. For the graft made with loops of single-ply material, 60 – 90 courses per inch are also found to be satisfactory.

If desired, the grafts may be provided with marking lines 17 to facilitate the avoidance of introduction of twist during stretching of the grafts in surgery.

It will thus be seen that the objects set forth above, among those made apparent from the preceding description, are efficiently attained and, since certain changes may be made in carrying out the above method and in the article set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A warp-knitted, double-velour synthetic vascular graft of a material to which tissue can adhere, comprising a tubular trellis of a non-texturized yarn, said trellis being provided with a multiplicity of knitted fibrous loops of a texturized yarn projecting both outwardly and inwardly from the surfaces of said trellis and presenting a pile mat of filamentary material receptive to tissue ingrowth on the outer and inner surfaces of said trellis, the ratio of the length of said loop yarn to the length of said trellis yarn in said graft lying between 1.75 and 4.50, said loops being effective to improve the rate of growth of tissue into said graft.

2. The synthetic graft of claim 1, in which said knitted tubular trellis has regular, circumferential corrugations along its length.

3. The synthetic graft of claim 1, wherein said graft is bifurcated.

4. The synthetic graft of claim 1, wherein said outwardly projecting loops are from three to 10 times as long as said inwardly projecting loops.

5. The synthetic graft of claim 1, wherein said outwardly projecting loops are from four to seven times as long as said inwardly projecting loops.

6. The synthetic graft of claim 1, wherein said graft is of a warp-knitted, locknit structure thereby making said tube extremely ravel-resistant.

7. The synthetic graft of claim 1, wherein said graft is of a warp-knitted, tricot structure, thereby making said tube extremely ravel-resistant.

8. The synthetic graft of claim 1, wherein said trellis is of a non-texturized single-ply yarn having a count of 30–150 denier.

9. The synthetic graft of claim 1, wherein said trellis is of a non-texturized single-ply yarn having a count of 30–70 denier.

10. The synthetic graft of claim 1, wherein said trellis is of a non-texturized single-ply yarn having a count of about 40 denier.

11. The synthetic graft of claim 1, wherein said trellis is of a non-texturized yarn of more than one ply having a total count of 30–150 denier.

12. The synthetic graft of claim 1, wherein said trellis is of a non-texturized yarn of more than one ply having a total count of 30–70 denier.

13. The synthetic graft of claim 1, wherein said trellis is of a non-texturized yarn of more than one-ply having a total count of about 40 denier.

14. The synthetic graft of claim 8, wherein said loops are of a texturized single-ply yarn having a count of 30–150 denier, the count being at least as large as that of said trellis.

15. The synthetic graft of claim 8, wherein said loops are of a texturized single-ply yarn having a count of 30–70 denier, the count being at least as large as that of said trellis.

16. The synthetic graft of claim 8, wherein said loops are of a texturized single-ply yarn having a count of about 40 denier, the count being at least as large as that of said trellis.

17. The synthetic graft of claim 8, wherein said loops are of a texturized double-ply yarn each ply of said double-ply yarn having a count of 30–150 denier, the count being at least as large as that of said trellis.

18. The synthetic graft of claim 8, wherein said loops are of a texturized double-ply yarn each ply of said double-ply yarn having a count of 30–70 denier, the count being at least as large as that of said trellis.

19. The synthetic graft of claim 8, wherein said loops are of a texturized double-ply yarn each ply of said double-ply yarn having a count of about 40 denier, the count being at least as large as that of said trellis.

20. The synthetic graft of claim 8, wherein said loops are of a texturized multi-ply yarn having a total count of 60–300 denier, said total count being at least as large as that of said trellis.

21. The synthetic graft of claim 8, wherein said loops are of a texturized multi-ply yarn having a total count of 60–140 denier, said total count being at least as large as that of said trellis.

22. The synthetic graft of claim 8, wherein said loops are of a texturized multi-ply yarn having a total count of about 80 denier, said total count being at least as large as that of said trellis.

23. The synthetic graft of claim 1, wherein said yarn is a polyester.

24. The synthetic graft of claim 17, wherein said yarn is Dacron.

25. The synthetic graft of claim 1, wherein said loops are of single-ply texturized yarn and the number of courses per inch in said graft is from 60–90, said graft being relatively high in porosity.

26. The synthetic graft of claim 1, wherein said loops are of two-ply texturized yarn and the number of courses per inch in said graft is from 60–90, said graft being relatively low in porosity.

27. The synthetic graft of claim 1, wherein said loops are of multi-ply texturized yarn and the number of courses per inch in said graft is from 60–90, said graft being relatively low in porosity.

28. The synthetic graft of claim 1, wherein said graft has thereon a marking line to aid in avoiding the introduction of twist in said graft during implantation.

29. The synthetic graft of claim 3, wherein said graft has thereon marking lines to aid in avoiding the introduction of twist in said graft during implantation.

30. The synthetic graft of claim 1, wherein said trellis is of a non-texturized yarn of at least one ply with a total count of 30–150 denier and said loops are of a texturized yarn of at least one ply with a total count of 30–300 denier, the total count of said loop yarn being at least as great as the total count of said trellis yarn.

* * * * *